United States Patent [19]

Gräser et al.

[11] 4,192,821

[45] Mar. 11, 1980

[54] PURIFICATION OF CRUDE MONOCHLOROMETHANE GAS

[75] Inventors: Reinhold Gräser, Frankfurt am Main; Wilhelm Lendle, Bad Soden am Taunus; Hendrik W. Post, Hofheim am Taunus, all of Fed. Rep. of Germany

[73] Assignee: Hoechst Aktiengesellschaft, Frankfurt am Main, Fed. Rep. of Germany

[21] Appl. No.: 862,382

[22] Filed: Dec. 20, 1977

[30] Foreign Application Priority Data

Dec. 22, 1976 [DE] Fed. Rep. of Germany ....... 2658132

[51] Int. Cl.$^2$ ............................................. C07C 19/00
[52] U.S. Cl. ................................. 260/652 P; 260/657
[58] Field of Search ......................................... 260/652 P

[56] References Cited

FOREIGN PATENT DOCUMENTS 1048209 11/1966 United Kingdom ................. 260/652 P

*Primary Examiner*—Delbert E. Gantz
*Assistant Examiner*—Joseph A. Boska
*Attorney, Agent, or Firm*—Curtis, Morris & Safford

[57] ABSTRACT

Crude monochloromethane is freed from dimethylether by a washing with aqueous hydrochloric acid.

4 Claims, No Drawings

PURIFICATION OF CRUDE MONOCHLOROMETHANE GAS

The present invention relates to the purification of crude monochloromethane gas.

Monochloromethane is nowadays preferably prepared by the hydrochlorination of methanol. The reason is that with the direct chlorination of methane, monochloromethane represents only one of the reaction products besides methylene chloride, chloroform and carbon tetrachloride.

In the technically preferred hydrochlorination of methanol in the gaseous phase, methanol and hydrogen chloride are reacted at about 5 bars and at a temperature in the range of from 280° to 350° C. in the presence of an aluminum oxide catalyst. The crude monochloromethane being formed shows after cooling for example approximately the following composition:

$CH_3Cl$: 98%
$CH_3OH$: <0.03%
$CH_3-O-CH_3$: 0.3-1.3%
$HCl$: <2%
$H_2O$: ~0.1%.

The gaseous crude monochloromethane is then usually washed with concentrated sulfuric acid.

In the course of this process the gas is dried to a residual content of less than 0.01% of water (which is due to the water vapor partial pressure of the sulfuric acid); the dimethylether is bound as oxonium compound, and the methanol is bound as sulfuric acid ester.

A recovery of these two compounds from the sulfuric acid, however, is only possible at a great expense and even then it will never be complete.

For example, with water vapor at 200° C. the dimethylether and the sulfuric acid methylester can only be stripped partly from the acid. The acid which has shown a dark-brown color prior to the stripping is thereafter deep black due to the separated carbon. Whether the washing sulfuric acid has been stripped in this manner or not, the working-up of the about 80% acid represents a difficult ecological problem which can only be solved satisfactorily by an industrial collective system where the acid is used again in another process.

There have been numerous attempts to solve the above-described difficulties by washing out the dimethylether as well as the methanol portion, which is only small in many cases, by a selective washing effected prior to the washing with sulfuric acid. In the literature a series of inorganic substances have been described which form addition products with dimethylether, such as $ZnCl_2$, $ZrCl_4$, $AlCl_3$, $FeCl_3$, $SnCl_4$, $TiCl_4$ and $CaCl_2$. If an aqueous solution of substances of this kind is used for a washing of the crude monochloromethane, the dimethylether is washed out as an addition product, and the methanol is washed out as an aqueous solution.

In German Patent Specification No. 599,691, for example, a method has been described according to which saturated zinc chloride solution is used for the absorption of dimethylether. As has been stated in said publication, about 1.5 kg of dimethylether can be absorbed by 1 liter of zinc chloride solution of the density $D_{25}=2.22$ at 0° C. By heating the zinc chloride solution at a temperature in the range of from 60° to 65° C., the dimethylether can be eliminated again.

All purification methods of this kind have the drawback, however, that a foreign substance has to be introduced into the system which affects the purity of the monochloromethane. In the case of washing solutions which are to be circulated with absorption and desorption, as for example zinc chloride solutions, hydrogen chloride would accumulate in the washing solution. Thereafter either the hydrogen chloride has to be eliminated prior to the washing of the crude monochloromethane, or a determined part of the washing solution must constantly be drawn off and replaced by fresh solution.

Surprisingly, it has now been found that crude monochloromethane which has been washed with about 32% hydrochloric acid contained only 1/10 or less of the dimethylether having been present before. It was still more surprising that only a small increase of the concentration of the washing hydrochloric acid results in a further reduction of the concentration of dimethylether in the monochloromethane. In the case of a hydrochloric acid having a content of 37% of hydrogen chloride, as is obtained in the isothermal absorption of hydrogen chloride in water, the dimethylether is washed out of the monochloromethane to an extremely high degree. Also, methanol could not be detected in the washed monochloromethane. The advantages of the novel process are obvious; above all, there is no need to introduce a new substance into the system. In the course of the distillation of the charged washing hydrochloric acid there is formed a gaseous mixture of hydrogen chloride, dimethylether, methanol and water vapor, and azeotropic hydrochloric acid as sump product. After drying, the above-mentioned gas mixture may be used again directly for the monochloromethane synthesis. From the azeotropic hydrochloric acid, washing hydrochloric acid can be prepared again by the absorption of hydrogen chloride.

A subsequent washing with sulfuric acid is only required for the drying of the monochloromethane.

The process of the invention for eliminating dimethylether from crude monochloromethane comprises washing the crude monochloromethane with aqueous hydrochloric acid.

If methanol is contained in the crude monochloromethane, it is at least partially removed, too, by the washing with hydrochloric acid.

The washing with hydrochloric acid is carried out generally at a temperature in the range of from 0° to 50° C. and a pressure of from 1 to 10 bars.

Preference is given to a hydrochloric acid having a concentration of more than 30%. A hydrochloric acid having a concentration of more than 35% is particularly preferred. The temperature of the washing hydrochloric acid should preferably be above the condensation temperature of the crude monochloromethane at the chosen reaction pressure.

When applying the process of the invention, the dimethylether formed as by-product of the monochloromethane synthesis can be recycled into the reactor and can be converted into monochloromethane in the following passage. The washing with sulfuric acid which is effected following the washing with hydrochloric acid of the crude monochloromethane yields a sulfuric acid which has only been diluted by the water absorbed. It may therefore be used again for the drying of the monochloromethane, optionally after a partial dehydration, however, without a complicated purification.

The following Examples serve to illustrate the invention.

EXAMPLE 1:

In a bubble plate column with 20 plates, 200 l/h of crude monochloromethane having a content of from 0.51 to 0.55% of dimethylether were washed continuously with 5 l/h of 32% hydrochloric acid in the countercurrent. The average absorption temperature was 20° C. The content of dimethylether in the washed gas was in the range of from 0.032 to 0.030%.

EXAMPLE 2:

In a bubble plate column as described in Example 1, 450 l/h of crude monochloromethane having a content of 0.684% of dimethylether were washed continuously with 14 l/h of 31.5% hydrochloric acid at 10° C. The content of dimethylether in the washed gas was 0.012%.

EXAMPLE 3:

In a bubble plate column as described in Example 1, 200 l/h of crude monochloromethane having a content of from 1.33 to 1.5% of dimethylether were washed continuously with 5 l/h of 37.9% hydrochloric acid. The absorption temperature was 22° C. on an average. The residual content of dimethylether following the washing was in the range of from 0.0006 to 0.0034%.

EXAMPLE 4:

In a bubble plate column as described in Example 1, 200 l/h of crude monochloromethane having a content of from 0.57 to 1.12% of dimethylether were washed continuously with 5 l/h of 37.2% hydrochloric acid. The average absorption temperature was 20° C. A residual content of 0.0004% of dimethylether was measured in the washed gas.

What is claimed is:

1. A process for the elimination of dimethylether from crude monochloromethane, consisting essentially of monochloromethane and dimethylether which comprises washing the crude monochloromethane with aqueous hydrochloric acid of a concentration greater than 35%.

2. A process as claimed in claim 1, wherein the temperature of the aqueous hydrochloric acid is above the condensation temperature of the crude monochloromethane at the reaction pressure.

3. A process as claimed in claim 1, which comprises carrying out the washing at a temperature in the range of from 0° to 50° C.

4. A process as claimed in claim 1, which comprises carrying out the washing at a pressure of from 1 to 10 bars.

* * * * *